United States Patent
Khalili

(10) Patent No.: US 8,016,885 B2
(45) Date of Patent: Sep. 13, 2011

(54) CERVICAL MOTION PRESERVATION DEVICE

(75) Inventor: Farid Bruce Khalili, Briarcliff Manor, NY (US)

(73) Assignee: Altus Partners, LLC, Newtown Square, PA (US)

( * ) Notice: Subject to any disclaimer, the term of this patent is extended or adjusted under 35 U.S.C. 154(b) by 648 days.

(21) Appl. No.: 11/337,418

(22) Filed: Jan. 23, 2006

(65) Prior Publication Data

US 2007/0173937 A1 Jul. 26, 2007

(51) Int. Cl.
*A61F 2/44* (2006.01)

(52) U.S. Cl. ............................ 623/17.11; 623/17.15

(58) Field of Classification Search ..... 623/17.11–17.16
See application file for complete search history.

(56) References Cited

U.S. PATENT DOCUMENTS

| | | | | |
|---|---|---|---|---|
| 5,674,296 A * | 10/1997 | Bryan et al. | ................ | 623/17.16 |
| 6,001,130 A * | 12/1999 | Bryan et al. | ................ | 623/17.16 |
| 6,146,421 A * | 11/2000 | Gordon et al. | ............. | 623/17.15 |
| 6,235,059 B1 * | 5/2001 | Benezech et al. | .......... | 623/17.16 |
| 6,682,563 B2 * | 1/2004 | Scharf | ........................ | 623/17.16 |
| 6,972,037 B2 * | 12/2005 | Zubok et al. | ................ | 623/17.15 |
| 6,972,038 B2 * | 12/2005 | Zubok et al. | ................ | 623/17.15 |
| 6,994,728 B2 * | 2/2006 | Zubok et al. | ................ | 623/17.15 |
| 6,994,729 B2 * | 2/2006 | Zubok et al. | ................ | 623/17.15 |
| 6,997,954 B2 * | 2/2006 | Zubok et al. | ................ | 623/17.15 |
| 6,997,955 B2 * | 2/2006 | Zubok et al. | ................ | 623/17.15 |
| 7,175,662 B2 * | 2/2007 | Link et al. | .................... | 623/17.11 |
| 7,198,643 B2 * | 4/2007 | Zubok et al. | ................ | 623/17.15 |
| 7,226,452 B2 * | 6/2007 | Zubok et al. | .................... | 606/99 |
| 7,566,346 B2 * | 7/2009 | Kirschman | ................ | 623/17.14 |
| 7,594,931 B2 * | 9/2009 | Louis et al. | ................ | 623/17.11 |
| 2002/0128715 A1 * | 9/2002 | Bryan et al. | ................ | 623/17.15 |
| 2002/0143399 A1 * | 10/2002 | Sutcliffe | .................... | 623/17.11 |
| 2003/0167091 A1 * | 9/2003 | Scharf | ........................ | 623/17.11 |

* cited by examiner

*Primary Examiner* — Eduardo C Robert
*Assistant Examiner* — Ellen C Hammond
(74) *Attorney, Agent, or Firm* — Matthew B. Dernier, Esq.; Gibson & Dernier LLP

(57) ABSTRACT

A system of reconstruction for a spinal joint is directed to a modular implant assembly that includes an upper part and a lower part. The upper and lower parts each comprise a unitary body having an approximately ninety degree bend defining vertical and horizontal components. Each vertical component has a fastener hole for attaching it to a bone segment using a bone fastener. The horizontal sections each have a complementary contact surfaces in order to transmit compressive load therebetween and to accommodate sliding and pivoting relative movement therebetween. The vertical sections of each of the upper and lower part are offset with respect to a vertical centerline so that successive assemblies bridging more than one adjacent vertebral space can have an upper part and a lower part according to the present invention coexist on a single vertebra in a space-efficient manner wherein the vertical sections nest spatially.

4 Claims, 9 Drawing Sheets

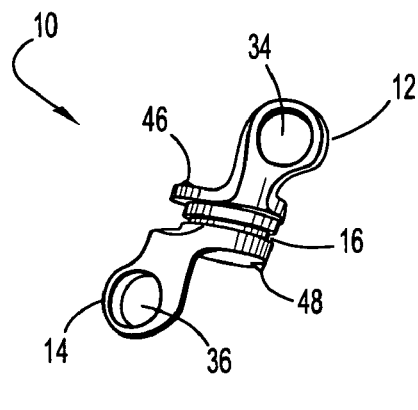
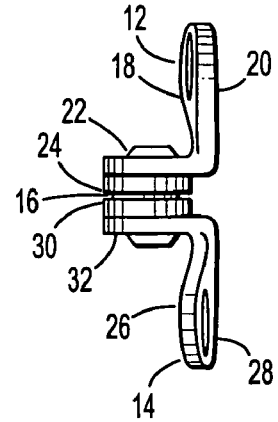
FIG. 1  FIG. 2
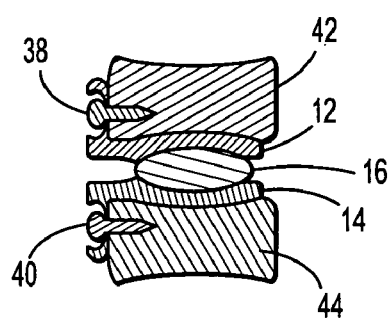
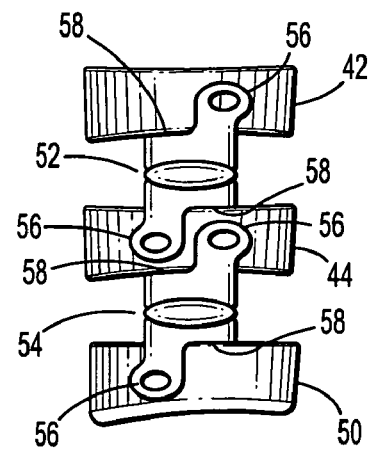
FIG. 3  FIG. 4

CERVICAL MOTION PRESERVATION DEVICE

RELATED APPLICATIONS

None.

TECHNICAL FIELD

The present invention relates to implantable artificial joint assemblies and, more particularly, to a joint assembly that allows a predetermined amount of desired motion to a joint and that is particularly well suited for use in restructuring a spinal disc section of a spine including, but not limited to, the cervical region.

BACKGROUND OF THE INVENTION

In orthopedics it is known to use various types of reconstruction assemblies to repair bone joints that have become deteriorated, damaged or degenerative, such as due to trauma or disease. Some reconstructions involve the use of various components such as bone screws, plates, bone grafts, fusion implants and other components. Depending on the type and method of reconstruction selected, complete stabilization with no movement may be selected, or a predetermined amount of controlled movement may be selected. In one technique of spinal reconstruction, for example, fusion of adjacent vertebrae is achieved using one or more plates fastened to adjacent vertebral segments in order to join the vertebral segments in a predetermined relationship for stabilization, sometimes installing a fusion device such as an implant or bone graft.

While complete fusion and, thus, resultant loss of movement between adjacent vertebrae is sometimes prescribed, fusion does limit movement and in the long term may adversely affect the disc adjacent to the fused joint by imposing heightened stress and wear. An alternative to fusion using motion preservation devices restore significant motion and disc space height which minimizes stress concentrations and pain.

The various known systems for allowing controlled movement of joint reconstructions have shortcomings. Such shortcomings include lack of versatility so as to require multiple configurations and sizes of hardware on hand during surgery; prohibitively complex or expensive components; lack of anatomical correspondence with resultant poor fit; high stress concentrations and unnatural load forces on adjacent or fused bone segments; and other shortcomings. Known motion preservation devices are generally restricted to only very stable constructs and degenerative disc disease cases, which is only 5%-10% of all cases.

Known designs include an insert that is positioned between adjacent vertebrae and that contacts the vertebrae only on the end plates, where the load is transferred in an axial direction parallel to the axis of the vertebral column. Such designs do not provide adequate initial stability and thus are subject to, for example, lateral slide out of the insert. In some cases this problem could be addressed by implementing additional components such as plates or artificial ligaments, thereby increasing cost, complexity, surgery time, and invasiveness.

Other known designs include structures having sections that overlap end faces of adjacent vertebrae, but do not transfer axial load from the end faces. Instead, they have additional sections that are fastened to anterior or other portions of the vertebrae using bone screws or similar means, thereby supporting the load via the screws and the interior sections. This type of system not only causes high stress concentrations in and around the bone screws and their anchoring points in the vertebrae that are at risk for failure under load, but such a system prevents or shields axial load transfer through the end plates. By preventing load through the end plates, bone ongrowth is significantly prevented.

Various known assemblies require a variety of sized sets to be on hand during surgery so that a surgeon can make a determination during the procedure as to which size will be best suited for a patient. This adds to the cost or reduces the versatility of the known assemblies.

Various known assemblies require a relatively large amount of surface area of a vertebra to the extend that constructing multiple, adjacent levels of reconstructed vertebrae (i.e., spanning two or more adjacent vertebral disc spaces) is prohibited simply because there is not enough space to install all of the components required. Other known designs include keel sections that are placed into channels cut into vertebral end faces. Such keel designs are subject to increased risk of cross-fracture of the vertebrae because they require channels to be cut which remove bone material crucial to structural integrity, and they often leave no room for additional implants such as on the opposite side of a vertebra.

OBJECTS OF THE INVENTION

It is an object of the present invention to provide a joint reconstruction system that overcomes the above-mentioned shortcomings and that achieves additional, inherent objectives apparent from the description set forth below.

It is a further object of the present invention to provide a joint reconstruction system particularly well suited, as described with respect to the preferred embodiments, for cervical spinal reconstruction where assemblies are constructed across more than one adjacent, or successive, vertebral spaces. These and other objects are described below or are inherent with respect to the present invention.

SUMMARY OF THE INVENTION

The present invention is described in the preferred embodiments as directed to a system of reconstruction for a spinal joint. It is understood, however, that the present invention is not limited to spinal reconstruction and, as understood by one skilled in the art,m may be adapted for application to other types of joints.

A preferred embodiment is directed to a three-piece, modular implant assembly that includes an upper part, a lower part, and a center core. The upper part and the lower part are identical in size and shape, though they could differ somewhat if desired or necessary. Each of the upper and the lower parts comprise a unitary body having an approximately ninety degree bend in it defining vertical and horizontal sections. The vertical section is preferably offset to one side of the vertical centerline (for reasons discussed below) and has at least one fastener hole to accommodate a fastener such as a bone screw. The hole may be slotted to allow predetermined sliding relative to a bone-screw and/or it may be shaped to allow pivoting relative to a bone-screw in instances where resultant freedom of movement of adjacent vertebrae is desired. This may be altered to a desired degree. The horizontal section has on its side facing toward the vertical section a vertebral end-face contacting surface that may be contoured and/or have projections to engage and hold securely to vertebral end faces, as well as to transfer axial load from the end faces. It may have a convex shape to it that fits and mates with the natural anatomy of the end faces to maximize surface contact area and to maximally distribute load. The side of the horizontal section facing away from the vertical section has a generally concave surface that is adapted to pivotally engage a center core of generally spherical shape. The lower part is preferably an inverted copy of the upper part so that its surfaces engage the center core and the lower adjacent vertebrae in a manner as described above with respect to the upper part. The vertical sections of each of the upper and lower parts have at least one fastener hole to enable a fastener such as a bone screw to fasten the respective part to a respective vertebra. The hole may be oversized, slotted or otherwise configured to allow relative movement of the screw and the part, thereby facilitating controlled movement of adjacent vertebrae.

An alternate preferred embodiment is directed to utilizing one of either the upper part of the lower part in a configuration as described above, but combining the center core with the other part for a total of two parts instead of three.

BRIEF DESCRIPTION OF THE DRAWINGS

FIG. 1 is a front, perspective view of a preferred embodiment of the present invention.

FIG. 2 is a side view of the preferred embodiment as shown in FIG. 1.

FIG. 3 is a front view of the preferred embodiment of FIG. 1 shown assembled to adjacent vertebrae.

FIG. 4 is a side view of the preferred embodiment of the present invention shown assembled to adjacent vertebrae.

DESCRIPTION OF THE PREFERRED EMBODIMENTS

Figure 5:
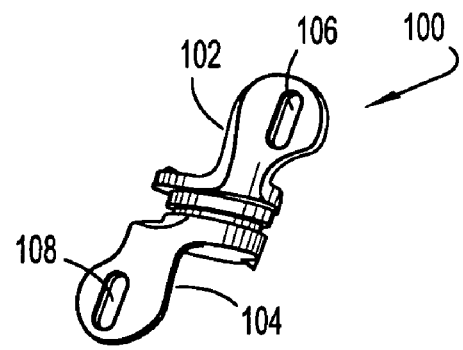
FIG. 5 is a front view of a second preferred embodiment of a component of the present invention.

A first embodiment assembly according to the present invention is described with respect to FIGS. 1-4. An implant assembly (10) according to the present invention comprises an upper part (12), a lower part (14), and a center core (16). The upper part (12) comprises a vertical section front face (18), a vertical section rear face (20), a horizontal section top face (22), and a horizontal section bottom face (24). The lower part (14) comprises a vertical section front face (26), a vertical section rear face (28), a horizontal section top face (30), and a horizontal section bottom face (32). Each of the vertical sections of the upper part (12) and the lower part (14) comprise at least one fastener hole (34, 36). Each hole (34, 36) is adapted to receive a fastener (38, 40) such as a bone screw.

The horizontal top face (22) of the upper part (12) and the horizontal bottom face (32) of the lower part (14) are each preferably convex in shape to match the anatomical shape of the end faces of adjacent vertebrae (42, 44) for optimal load distribution. One or more teeth (46, 48) or similar protrusions are provided to enhance grip of to bite into the end faces of the vertebrae. The opposite sides of the horizontal sections, namely the horizontal bottom face (24) of the upper part (12) and the horizontal top face (30) of the lower part (14), face each other and are generally concave shaped to pivotably engage a center core (16) that is convex on upper and lower surfaces and, as such, may be generally spherically shaped. Depending on the specific dimensions of the concave and convex portions, as well as on any raised circumferential rims (not shown) that may be provided on the faces (24, 30) or a flange (not shown) that may be provided on the center core (16), pivotal movement may be controlled to a certain degree. Similarly, predetermined sliding movement of the center core (16) relative to the upper and lower parts (12, 14) may be introduced if desired by adjusting such dimensions and flange or rim features.

The bone screws (38, 40) or fasteners may be of a known type having heads that are sized to adequately hold the parts (12, 14) to adjacent vertebrae but that allow predetermined sliding movement within the holes (34, 36) and/or that allow relative pivoting within the holes (34, 36). These features allow predetermined movement or dynamization of an assembled vertebral section using the present invention system. As shown in the preferred embodiment, the holes (34, 36) are oversized relative to the screw shafts to allow sliding and pivoting, and the screws (38, 40) have semi-spherical heads. By selecting hole size and/or head shape, one or both of sliding and pivoting movement can be controlled or eliminated if desired.

As shown in FIG. 4, more than two adjacent vertebrae (42, 44, 50) may receive adjacent assemblies (52, 54) according to the present invention. This in because the offset allows a single vertebra to receive two assembly parts, thereby enabling the present invention assemblies to bridge adjacent vertebral spaces separated by only one vertebra. This is attributable to the offset or asymmetrical characteristic of positioning a vertical portion (56) offset from a vertical centerline of the assembly to have its vertical portion (56) be nested relative to the recessed portion (58). This is a significant advantage over known designs which do not leave adequate space to attach adjacent assemblies to a sequence of adjacent vertebrae. Such known designs cannot be installed to bridge successive vertebral spaces separated only one vertebra.

Implant assemblies according to the present invention are installed using procedural steps and techniques that are similar to current procedures and techniques used in implanting known cervical plates. Thus, an advantage of the present invention is that spine surgeons are already familiar with and skilled in the procedures and techniques needed to install the present invention system. The center core (16) can be made available in a variety of sizes and geometries that can be used with one or a few standard size upper and lower parts (12, 14) thereby enabling the present invention to be presented as a modular system and minimizing inventory requirements. This provides advantages of versatility and cost efficiency not attained by known devices.

A second embodiment of the present invention assembly (100) is shown in FIG. 5 having an upper part (102) and a lower part (104) in which respective fastener holes (106, 108) are elongated. Such elongation of the holes (106, 108) may b e used for relieving stress by allowing relative movement of the upper or lower part (102, 104) with respect to a fastener (not shown) which attaches the assembly (100) to bone structures. The elongated holes (106, 108) may also provide versatility in positioning with respect to limited fastener positions during installation. It is understood that such elongated or slotted holes (106, 108) may be provided on one or on both parts (104, 106) in any of the preferred embodiments described herein.

Figure 6:
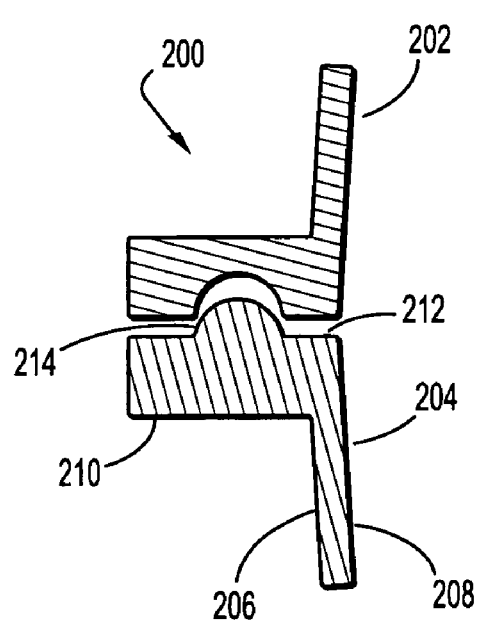
FIG. 6 is a side, cross-sectional view of a third embodiment of the present invention.

Another embodiment of the invention, shown in FIG. 6, is directed to an assembly (200) having an upper part (202) and a lower part (204). The upper part (202) is generally similar to the upper part (12) in the first preferred embodiment. The lower part (204) is comprised of a vertical front face (206), a vertical rear face (208), a horizontal lower face (210), and a horizontal upper face(212). The horizontal upper face (212) has a convex or dome portion (214) which, effectively, combines the lower part (14) and center core (16) of the first embodiment. The upper part (202), the lower part (204), or both, may be of various sizes, preferably interchangeable for compatibility with a variety of other parts, to allow versatility in mating parts.

Figure 7:
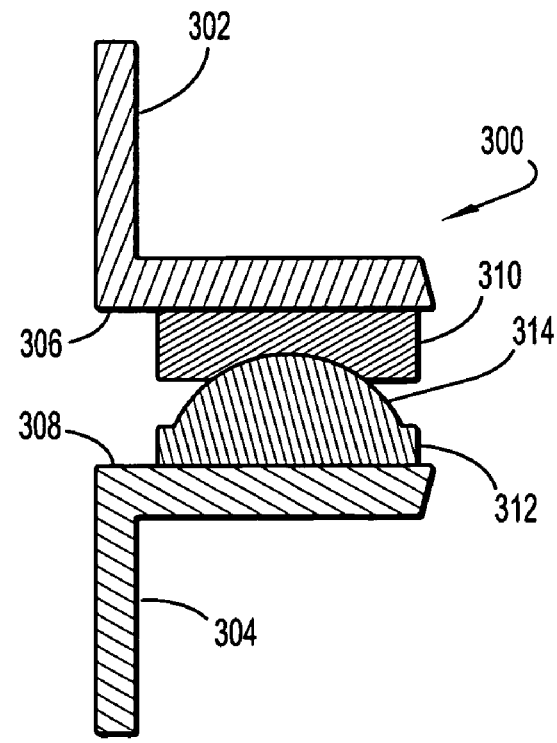
FIG. 7 is a side, cross-sectional view of a fourth embodiment of the present invention.

Another embodiment of the present invention, shown in FIG. 7, is directed to an assembly (300) having upper and lower parts (302, 304) generally similar to the upper and lower parts described in the earlier embodiments, but with flat, horizontal, opposing surfaces (306, 308). The flat surfaces (306, 308) are adapted to receive in a fixed manner inserts (310, 312) which cooperate to form a moveable joint. For example, the upper insert (310) has a concave surface for receiving a dome (312) portion of the lower insert (312). Variations of the specific insert geometries are contemplated.

In each embodiment of the present invention described herein, while the upper are lower parts are presented as identical in the above embodiments, except for one having a concave surface adapted to mate with a corresponding concave surface, it is conceivable that in some circumstances, such as those described below, non-like upper and lower parts can be utilized together in a system. Thus, with respect to FIGS. 8-9, another preferred embodiment is described herein and a component is referred to as a "first part" which could be used in a system with an identical "second part" or a non-like second part. Either part could be the upper or lower part depending on preference and conditions.

Figure 8:
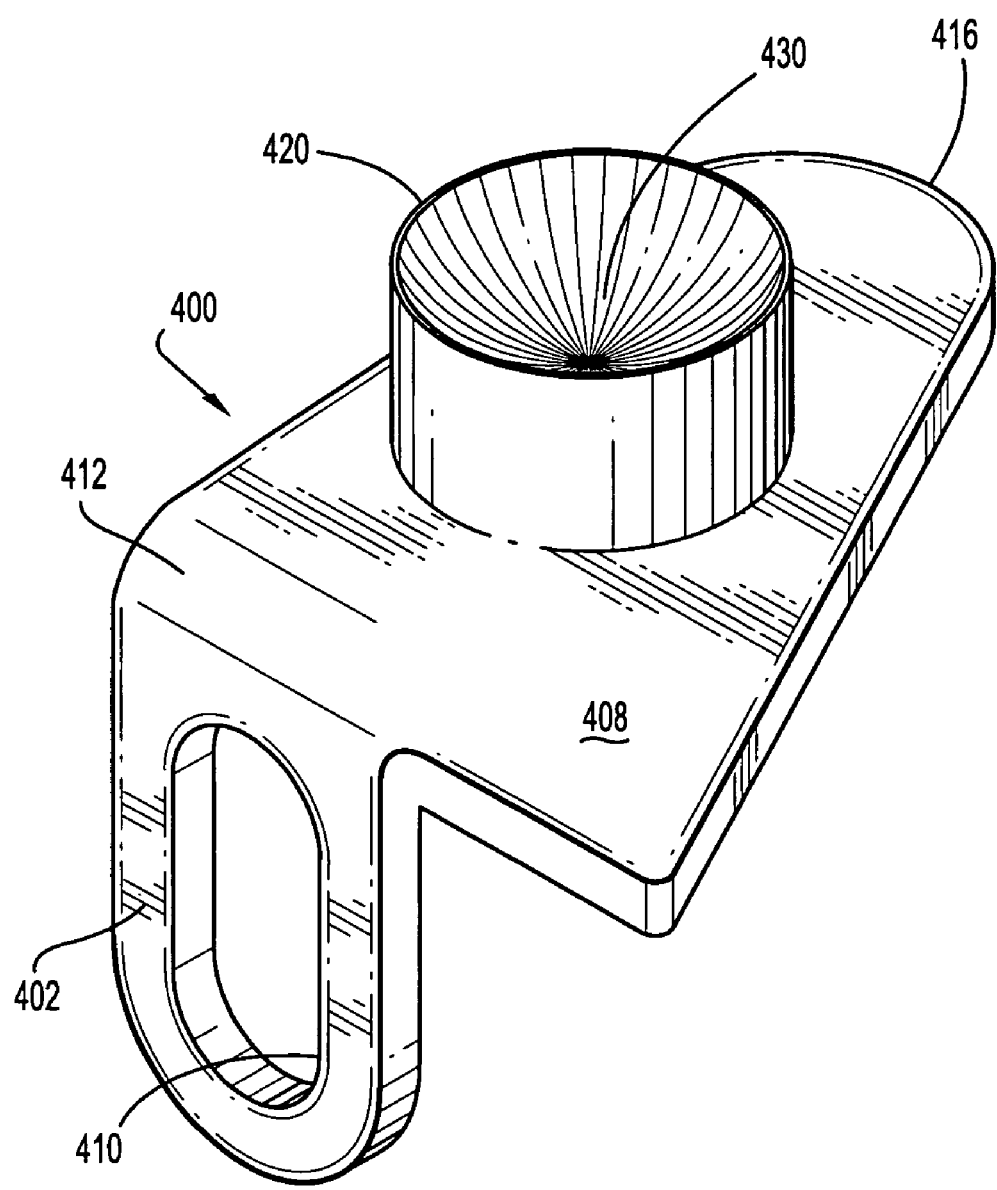
FIG. 8 is a perspective view of another preferred embodiment of a component of the present invention.
Figure 9A:
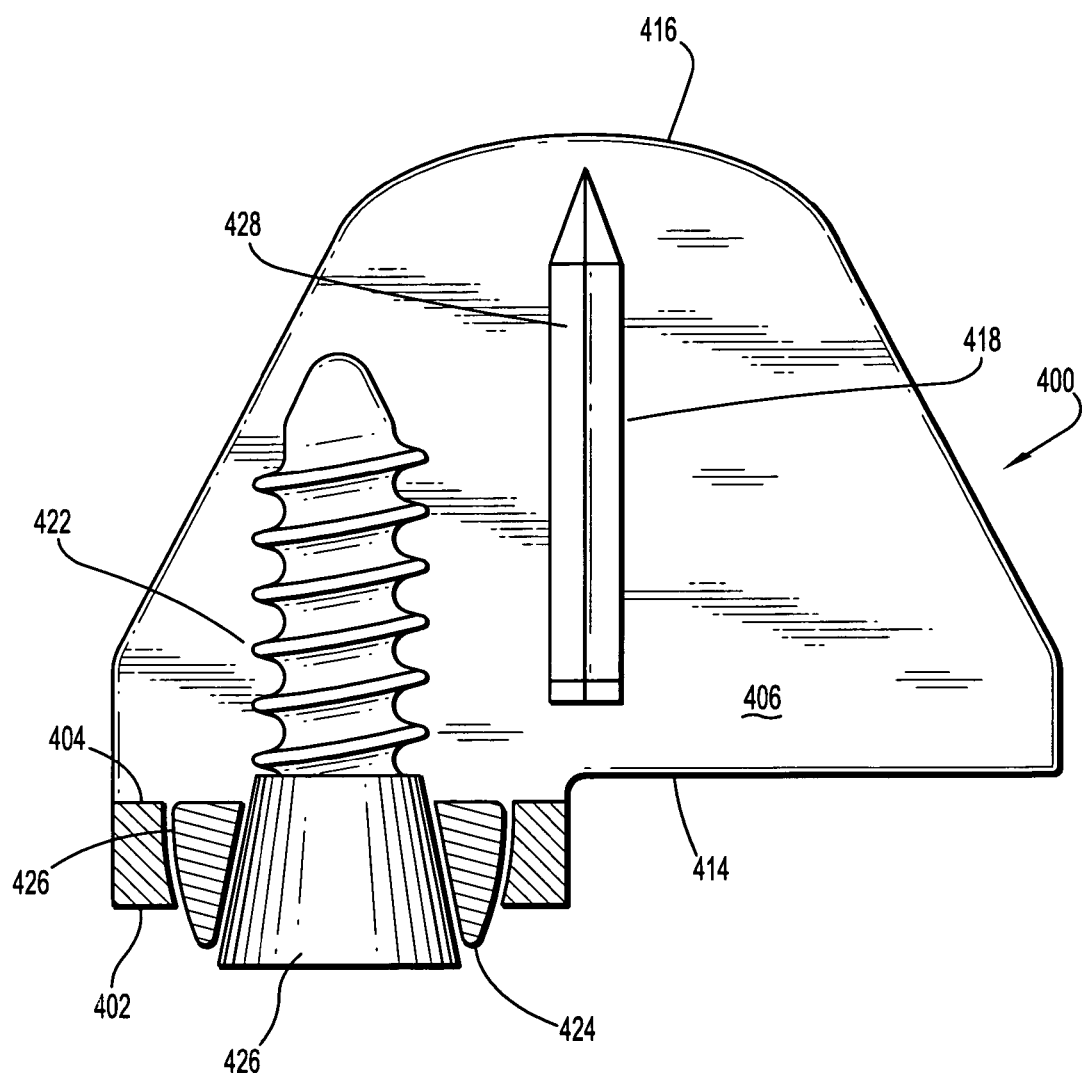
FIG. 9A is a top, partial cross-section view of a component according to an other embodiment of the present invention.
Figure 9B:
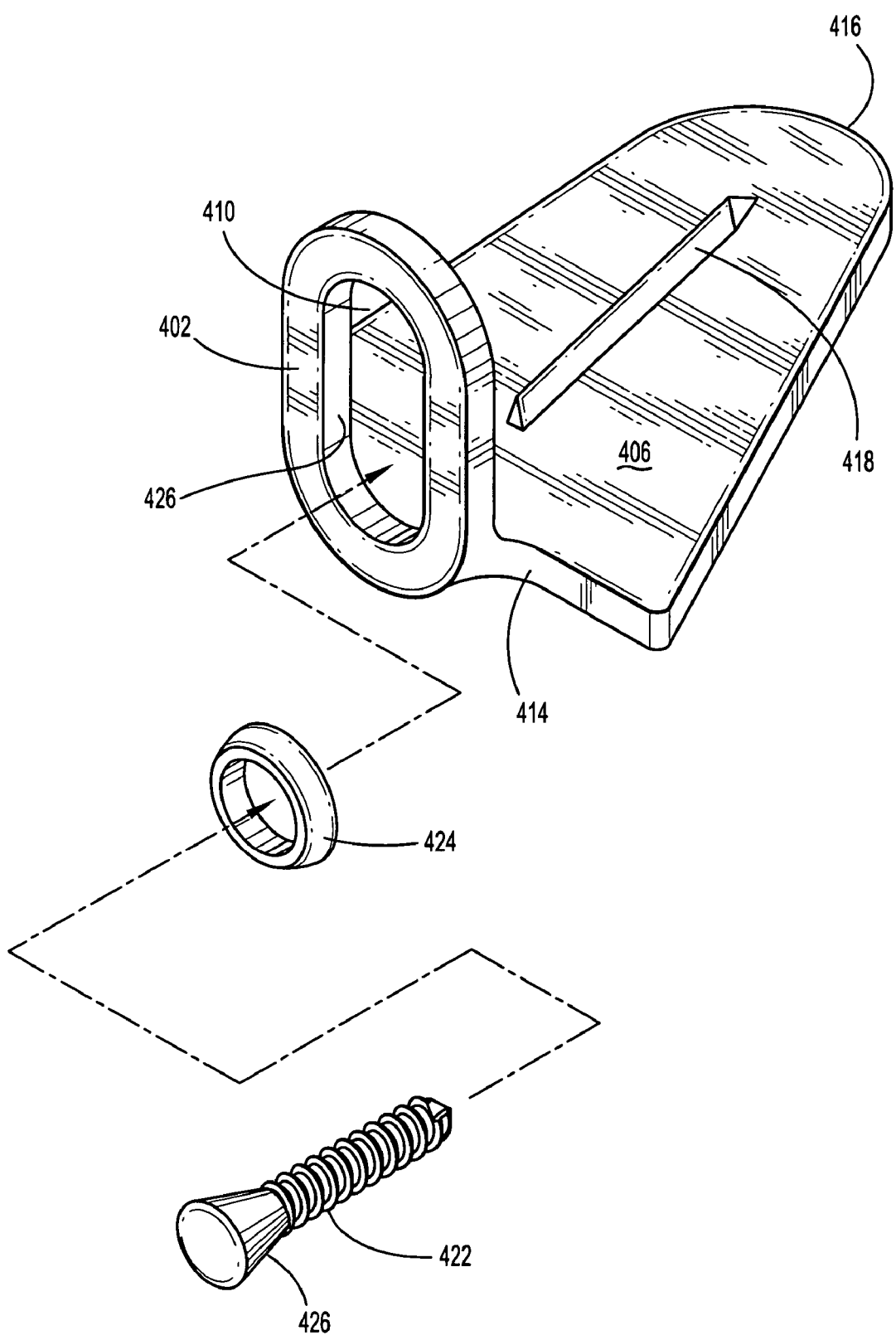
FIG. 9B is an exploded view of the component shown in FIG. 9A.

Thus, referring to FIGS. 8-9 (9A and 9B), a first part (400) has a generally vertical outward facing surface (402), a generally vertical inward facing surface (404), a generally horizontal interior surface (406), a generally horizontal exterior surface (408), a fastener hole (410), an approximately ninety degree bend region (412), an anterior side (414), a posterior side (416), a keel (418), and a sliding part (420). In the embodiment of FIGS. 8-9, the first part (400) is installed as part of a spinal implant assembly in a manner such as that described above with respect to the upper and lower parts of the preferred embodiments previously described. The horizontal surfaces (406, 408) are positioned in and intervertebral space and the vertical inward facing surface (404) contacts the anterior side of a vertebra. A bone faster or bone screw (422) passes through the hole (410) to secure the part (400) to the vertebra. Preferably, the bone screw (422) has a back-out prevention feature of any known type or of the type shown in FIG. 9 where a captive ring (424) resides in the hole (410) and is adapted to receive the head (426) of the bone screw (426) in a manner that causes the bone screw (424) to be held therein by an interference fit. The hole (410) may be slotted as shown in FIG. 8 to allow adjustment or to allow dynamic movement. The hole (410) and the screw head (426) may, as preferred, be provided with features (generally known) that enable pivotal movement or that restrict pivotal movement, depending on the desired application. The horizontal interior surface (406) may be provided with a keel (418) having a sharp edge (428) adapted to cut into the surface of a vertebral end face for stability. In the horizontal exterior surface (408), a sliding part (420) is provided. The sliding part (420) is one of a complementing pair of concave and convex surfaces. For illustration, in FIG. 8 there is shown a concave surface (430) which would slidingly and rotatably engage a complementing convex surface (not shown) on a second part (not shown) adapted to be mounted in the same intervertebral space and in contact with the opposing vertebra.

Figure 10:
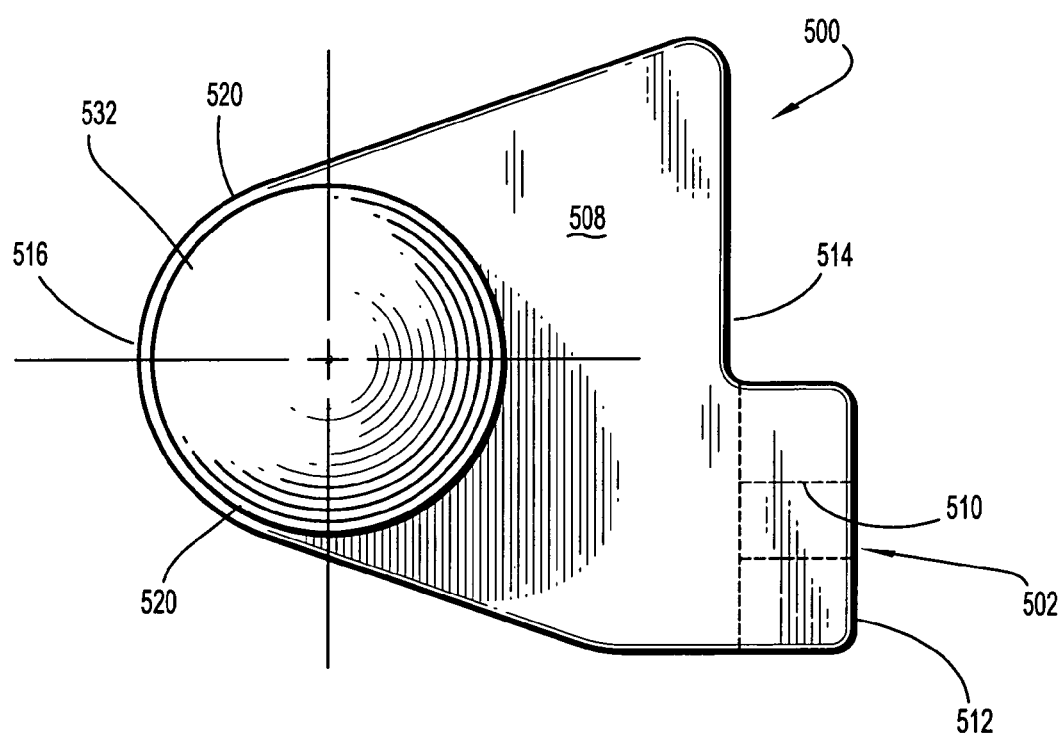
FIG. 10 is a bottom, schematic view of another component according to the present invention.

FIG. 10 is a view of a part (500) of the type that could be used in combination with the first part (400) of FIGS. 8-9. The part (500) is like first part (400) in all respects except that it has as its sliding part (520) a convex surface (532) adapted to slidingly and rotatably engage the concave surface (430) of first part (400). Below when reference to a feature is made as "not visible in FIG. 10" it means, in this context, that a different view than FIG. 10 is needed to see that feature. Since the part is the same as that illustrated in FIGS. 8-9 but for the "sliding part (520)", additional views are not shown because they would be redundant. The part (500) has a generally vertical outward facing surface (502), a generally vertical inward facing surface (not visible in FIG. 10), a generally horizontal interior surface (not visible in FIG. 10), a generally horizontal exterior surface (508), a fastener hole (shown in dotted lines as 410, but otherwise not visible in FIG. 10), an approximately ninety degree bend region (512), an anterior side (514), a posterior side (516), a keel (not visible in FIG. 10), and a sliding part (520). When selecting mating parts such as first part (400) and part (500) to be used together it would be preferable to select them with the vertical parts (i.e., 402 and 502) being offset to the same side so that they can nest as shown in and described with respect to FIG. 4.

Figure 11A:
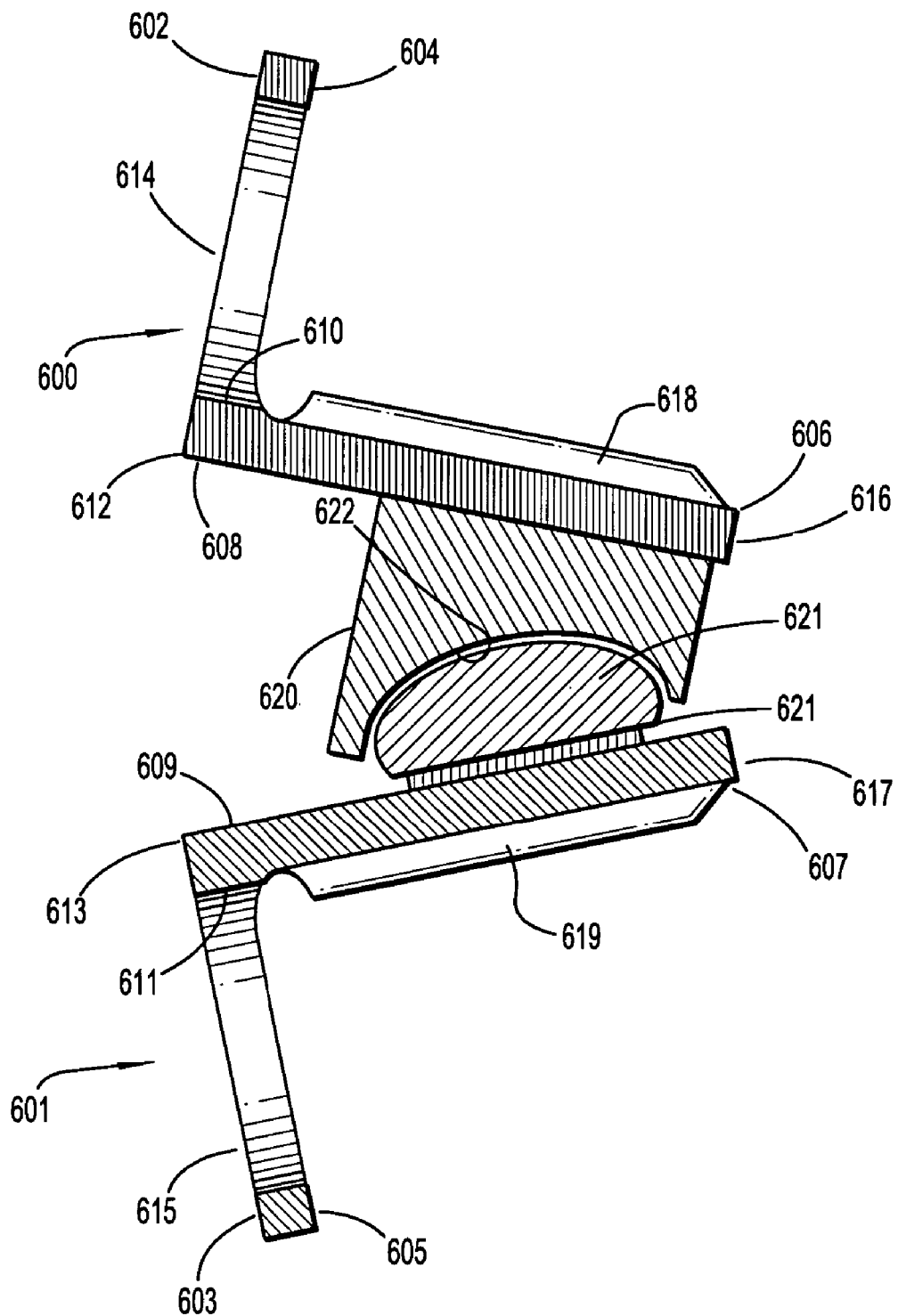
FIG. 11A is a cross-sectional, side view of another preferred embodiment assembly according to the present invention.
Figure 11B:
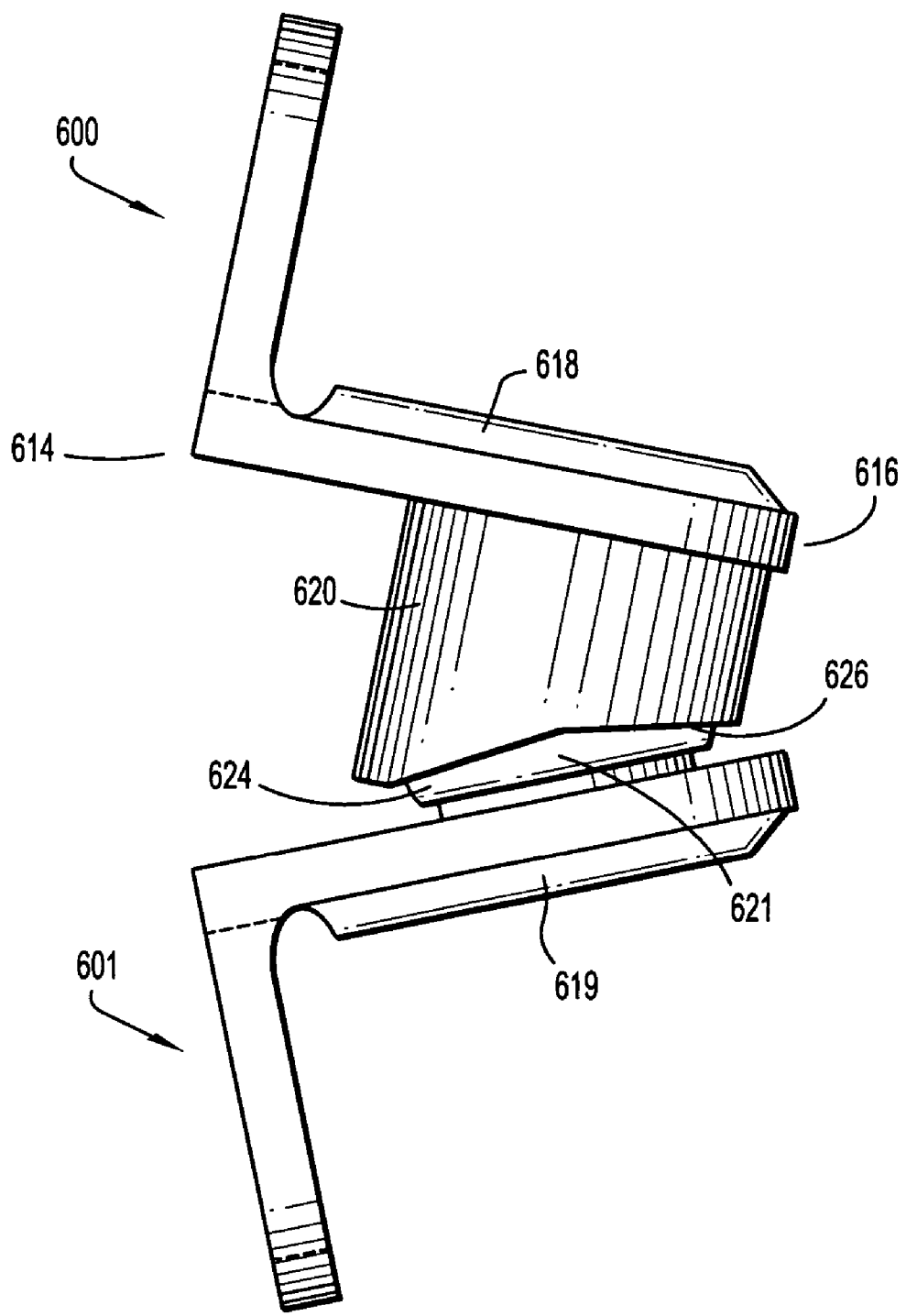
FIG. 11B is a side view of the assembly shown in FIG. 11A.

Another preferred embodiment is shown in FIGS. 11A-11B, FIG. 11A is shown in cross-section. In this embodiment, an assembly (600) of the type and for the purpose as described above with respect to preceding embodiments, has a first part (600) having a generally vertical outward facing surface (602), a generally vertical inward facing surface (604), a generally horizontal interior surface (606), a generally horizontal exterior surface (608), a fastener hole (610), an approximately ninety degree bend region (612), an anterior side (614), a posterior side (416), a keel (618), and a sliding part (620). A second part (601) has a generally vertical outward facing surface (603), a generally vertical inward facing surface (605), a generally horizontal interior surface (607), a generally horizontal exterior surface (609), a fastener hole (611), an approximately ninety degree bend region (613), an anterior side (615), a posterior side (617), a keel (619), and a sliding part (621).

The first part's sliding part (620) has a concave surface (622) adapted to slidingly and rotatably mate with a convex surface (621) on the second part (601). The first part's sliding part (620) has an angled sidewall first portion(624) and an angled sidewall second portion (626) providing a geometry that blocks over-rotation among the first part (600) and second part (601) relative to each other, but that allows more freedom of rotation in the posterior direction than in the anterior direction, in accordance with natural movements of a patient's spinal column, particularly in the cervical region.

Figure 12A:
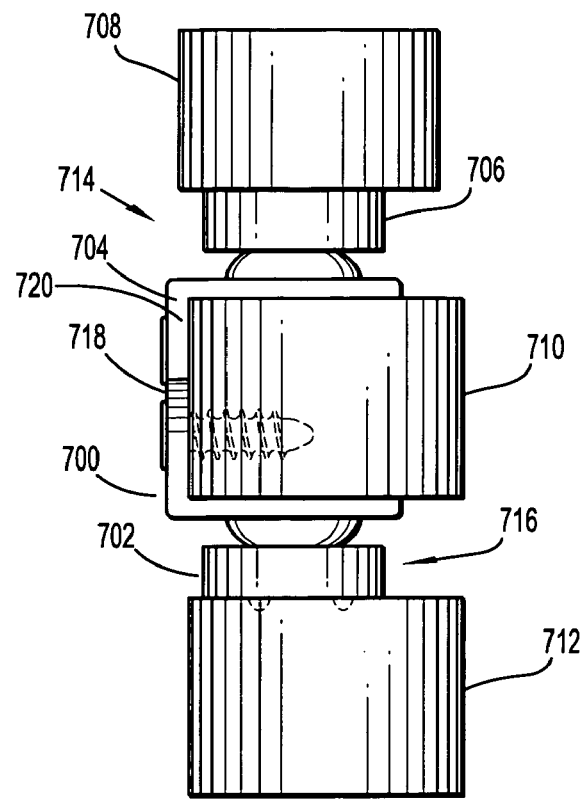
FIG. 12A is a schematic, side view of an assembly according to the present invention.
Figure 12B:
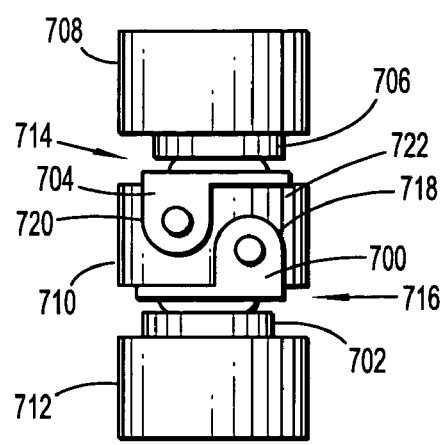
FIG. 12B is a schematic, front view of the assembly shown in FIG. 12A.

FIG. 12 illustrates, schematically, how a first part (700) intervertebral implant component according to present invention, can be used in cooperation with a non-like intervertebral component (702) of any type generally known that engages or cooperates with the first part (700) in a desirable and sufficient manner. For example, when two intervertebral assemblies (714, 716) are applied to adjacent intervertebral spaces defined by three successive vertebrae (708, 710, 712), a first part (700) according to any one of the above-described present invention embodiments is paired with a non-like intervertebral component (702) such as one generally known or one that does not have a vertical component (718, 720) of the type according to the present invention. This could be for any of a variety of reasons as determined by a surgeon. Likewise, a third part (704) according to the present invention is paired with a non-like fourth part (706). Due to the novel, offset vertical components (718, 720) of the present invention parts (700, 704), the vertical components nest as described with respect to the embodiment of FIG. 4, thereby making optimal use of limited space on the anterior face (722) of the vertebra (710) in the middle of the three-vertebrae sequence.

The upper parts, lower parts and center core from any of the above-identified embodiments may be made from any one of or a combination of known materials of sufficient strength and surgical compatibility for surgical implants. These materials include, but are not limited to, titanium, steel, ceramic, Teflon®, nylon, polyethylene, and Cobalt Chromium Moly.

While the preferred embodiments of the present invention have been described, various modifications can be made without departing from the scope of the invention.

What is claimed is:

1. An assembly for implantation into an intervertebral space between a first and a second vertebra, the assembly comprising:
   a pair of components, a first of the pair of components adapted to be inserted into the intervertebral space and in contact with a vertical face of the first vertebra and a second of the pair of components adapted to be inserted into the intervertebral space and in contact with a vertical face of the second vertebra; and
   a central core, pivotally engaged in the intervertebral space between the pair of components such that translational motion of the pair of components relative to each other is mitigated,
      wherein each component comprises:
         a first portion with a generally planar shape, with a surface thereof adapted for gripping an endface of the vertebra with which it is used and an opposing surface for engaging the central core; and
         a second portion, also with a generally planar shape, the second portion being oriented at about ninety degrees to the first portion and aligned substantially to one side of a centerline of the first portion, with a surface adapted to engage the vertical face of the vertebra with which it is used and,
      the second portions of the pair of components are arranged asymmetrically such that the second portion of the first of the components is offset relative to the second portion of the second of the pair of components along a centerline of the assembly normal to a plane parallel to the first portions of the pair of components and wherein the second portions of the pair of components are oriented away from each other such that each second portion extends from the respective first portion,
      the second portion is provided with a hole adapted for insertion of a fastener therethrough into the vertical face of a respective vertebra with which it is used, the hole is oversized relative to a shaft of the fastener to allow one or more of sliding or pivoting therein and a captive ring disposed in the hole, where the ring receives a head of the fastener in a manner that causes the fastener to be held therein.

2. The assembly of claim 1, further comprising:
   a convex face on the endface-engaging surface of the first portion; and
   a concave face on the opposing surface thereof.

3. The assembly of claim 1, wherein each second portion of the assembly is shaped to facilitate nesting with another second portion of another assembly attached to an opposite side of a vertebra bearing the assembly.

4. A system for reconstructing each of a pair of adjacent spinal joints, each spinal joint comprising a pair of vertebrae separated by an intervertebral space, the system comprising:
   two of the assemblies of claim 1, the first of the assemblies configured for implantation in the first intervertebral space and the second of the assemblies configured for implantation in the second intervertebral space, such that upon implantation of the two assemblies, the intermediate vertebra in the pair of the adjacent spinal joints will have one of the identical components fastened to each of the endfaces thereof.

* * * * *